United States Patent
Wang et al.

(10) Patent No.: US 11,814,519 B2
(45) Date of Patent: Nov. 14, 2023

(54) NITRIC OXIDE-RELEASING 3D-PRINTING COMPOSITIONS AND USES THEREOF

(71) Applicant: Virginia Commonwealth University, Richmond, VA (US)

(72) Inventors: Xuewei Wang, Henrico, VA (US); Hong Zhao, Glen Allen, VA (US); Yuanhang Yang, Richmond, VA (US); Wuwei Li, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 26 days.

(21) Appl. No.: 17/207,991

(22) Filed: Mar. 22, 2021

(65) Prior Publication Data
US 2021/0301135 A1    Sep. 30, 2021

Related U.S. Application Data

(60) Provisional application No. 63/000,130, filed on Mar. 26, 2020.

(51) Int. Cl.
| | |
|---|---|
| B33Y 70/00 | (2020.01) |
| C08L 83/04 | (2006.01) |
| B29C 64/112 | (2017.01) |
| B33Y 10/00 | (2015.01) |
| B33Y 80/00 | (2015.01) |
| C08G 77/08 | (2006.01) |
| C08K 5/43 | (2006.01) |
| C08K 3/01 | (2018.01) |

(Continued)

(52) U.S. Cl.
CPC ............ *C08L 83/04* (2013.01); *B29C 64/112* (2017.08); *B33Y 10/00* (2014.12); *B33Y 70/00* (2014.12); *B33Y 80/00* (2014.12); *C08G 77/08* (2013.01); *C08K 3/01* (2018.01); *C08K 5/43* (2013.01); *A61L 2300/20* (2013.01); *C08K 3/042* (2017.05); *C08K 3/346* (2013.01); *C08K 3/36* (2013.01); *C08K 2201/011* (2013.01)

(58) Field of Classification Search
None
See application file for complete search history.

(56) References Cited

U.S. PATENT DOCUMENTS

| | | | |
|---|---|---|---|
| 6,841,166 B1 * | 1/2005 | Zhang | A61L 33/0041 424/443 |
| 9,884,943 B2 * | 2/2018 | Frost | A61L 29/085 |

(Continued)

OTHER PUBLICATIONS

Colletta et al. "S-Nitroso-N-acetylpenicillamine (SNAP) impregnated silicone foley catheters: a potential biomaterial/device to prevent catheter-associated urinary tract infections." ACS biomaterials science & engineering 1.6 (2015): 416-424. (Year: 2015).*

(Continued)

*Primary Examiner* — Robert S Loewe
(74) *Attorney, Agent, or Firm* — WCF IP

(57) ABSTRACT

A nitric oxide-releasing 3D printing ink is described for its composition and uses in fabricating a plurality of types of nitric oxide-releasing medical devices. The printing ink composition comprises a mixture of at least one nitric oxide donor and at least one polymer. The nitric oxide-releasing medical device is manufactured by 3D printing technology and provides antimicrobial and/or antithrombus effects by releasing nitric oxide in the presence of moisture.

39 Claims, 7 Drawing Sheets

(51) Int. Cl.
   *C08K 3/34* (2006.01)
   *C08K 3/36* (2006.01)
   *C08K 3/04* (2006.01)

(56) References Cited

U.S. PATENT DOCUMENTS

| | | | |
|---|---|---|---|
| 2004/0224868 A1* | 11/2004 | Meyerhoff | A61K 33/34 510/320 |
| 2009/0004243 A1* | 1/2009 | Pacetti | A61L 31/10 514/315 |
| 2009/0233873 A1* | 9/2009 | Smith | A61P 7/02 568/11 |
| 2010/0303891 A1* | 12/2010 | Lee | A61K 47/58 424/78.37 |
| 2011/0059036 A1* | 3/2011 | Arnold | C08G 64/12 525/50 |
| 2011/0151000 A1* | 6/2011 | Schultz | A61L 31/16 424/490 |
| 2011/0159116 A1* | 6/2011 | Reynolds | A61K 33/00 423/405 |
| 2017/0174827 A1* | 6/2017 | Gu | A61L 27/54 |

OTHER PUBLICATIONS

Hopkins. et al. "Achieving long-term biocompatible silicone via covalently immobilized S-nitroso-N-acetylpenicillamine (SNAP) that exhibits 4 months of sustained nitric oxide release." ACS applied materials & interfaces 10.32 (2018): 27316-27325. (Year: 2018).*

Gierke et al. "S-Nitroso-N-acetyl-D-penicillamine covalently linked to polydimethylsiloxane (SNAP-PDMS) for use as a controlled photoinitiated nitric oxide release polymer." Science and technology of advanced materials (2011). (Year: 2011).*

Brisbois J., et al. "Long-term nitric oxide release and elevated temperature stability with S-nitroso-N-acetylpenicillamine (SNAP)-doped Elast-eon E2As polymer." Biomaterials 34.28 (2013): 6957-6966. (Year: 2013).*

* cited by examiner

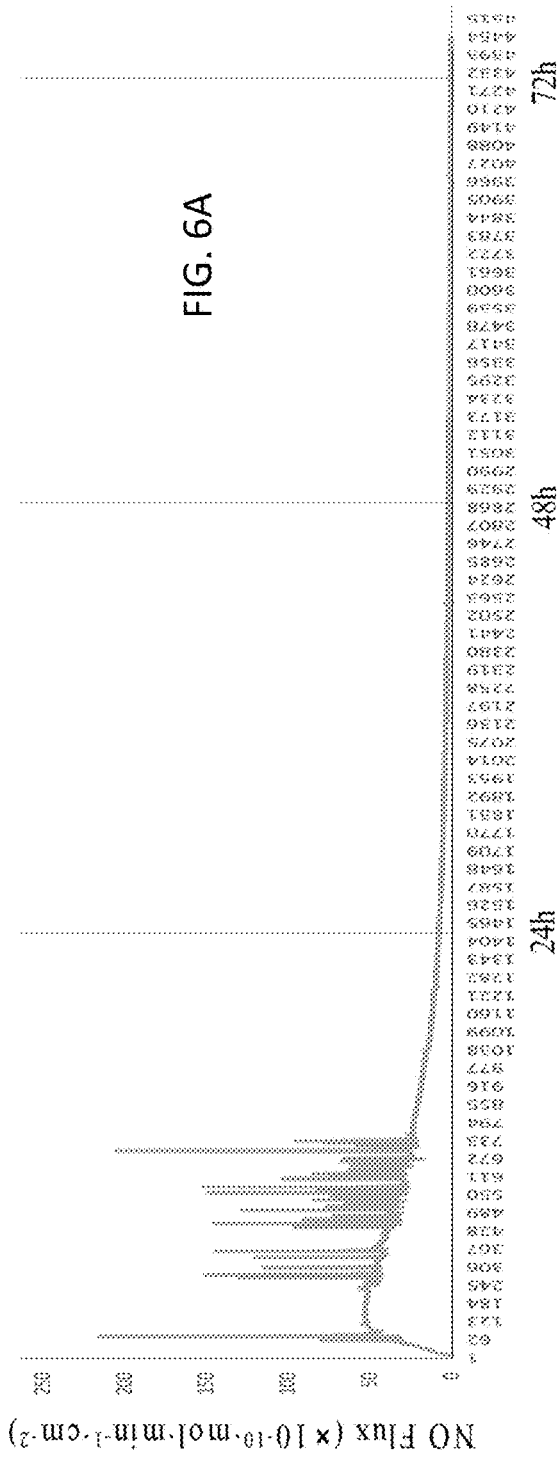

NITRIC OXIDE-RELEASING 3D-PRINTING COMPOSITIONS AND USES THEREOF

CROSS-REFERENCE TO RELATED APPLICATIONS

This application claims priority to U.S. Provisional Application 63/000,130 filed on Mar. 26, 2020. The complete content thereof is herein incorporated by reference.

FIELD OF THE INVENTION

The disclosure generally pertains to nitric oxide donor containing 3D printer ink compositions and methods of using such compositions to manufacture nitric oxide-releasing medical devices.

BACKGROUND

Medical implants and biomedical devices provide convenience and usefulness for modern medical intervention but many of them are associated with a serious risk of healthcare associated conditions, including infections. According to the U.S. Centers for Disease Control and Prevention (CDC) report, approximately 1 out of every 31 U.S. hospitalized patients develop one or more hospital-acquired infections (HAIs) on any given day. The HAIs (i.e., device-associated infections, surgery site infections, etc.) increase direct medical cost in U.S. up to 10 billion annually. Some exemplary types of device-associated infections include central line-associated bloodstream infections, catheter-associated urinary tract infections, and ventilator-associated pneumonia. Generally, bacteria can attach to medical devices even under the most sterile conditions and may further develop into a biofilm that is recalcitrant to antibiotics treatment. Various strategies for bacterial biofilm-resistance modifications have been investigated, such as applying antifouling coating or silver or nitric oxide coating and/or antibiotic coating onto the surface of the medical devices. However, those strategies were unsatisfactory in terms of reaching acceptable efficacy and long-term protection. Reduction of such infections through anti-infective surface modification of medical devices is challenging due to the broad spectrum of bacteria. In addition, the rapid emergence of antimicrobial resistance due to the prolonged use of antibiotics is further limiting treatment options.

Current strategies of incorporating anti-infective agents into medical devices generally involve three approaches. One is to apply a coating around the external surface of the device. In the coating method, the nitric oxide donor solutions are applied onto the surface of a device. U.S. Pat. No. 8,086,313 (Singhal) discloses a medical device with anti-infective agent coating in which the external surface of the medical device is coated with a lubricious material and/or an anti-infection agent. Another method is a solvent swelling-based bulk impregnation of a device. In this case, the anti-infective agent is dissolved in the solvent, and the pre-manufactured medical device (e.g., catheter made of silicone) is immersed in the solution to make the anti-infective imbibed final product.

Such strategies, however, do not provide solutions for some known concerns caused by coating the surface or impregnating the agents in pre- or post-manufacturing stages; e.g., unevenly coated surface providing bacterial growth platform, insufficient layer of coating, limited amount of agent into the device, de-lamination of coating, poor adhesion, short-term emission, etc. Generating an even coating in a solution is particularly challenging for the medical devices with complex shapes. In this case, a thin and uneven coating may be produced which limits the amount of released anti-infective agent. On the other hand, in the impregnation method, either at pre- or post-manufacturing stage of the medical device, only the agents that are capable of migrating through the base material (e.g., silicone or other polymers) may be used. Most antimicrobials, such as penicillin, cephalosporins, gentamicin and vancomycin are not compatible with this method, as the agents are not soluble in the usual swelling solvents and are not capable of migrating through polymer materials. In addition, swelling of the polymer typically changes the mechanical or surface property of the original devices. More importantly, many nitric oxide donors such as the endogenous s-nitrosoglutathione, cannot be dissolved in a solvent that swells the polymer. Other shortcomings from this approach include: i) requiring of excessive solvents or anti-infective agents; ii) increased swelling, drying, and/or manufacturing time; and iii) difficulty in production due to inaccessibility to the required complex machineries.

Thus, there is a need in the art for improved HAI prevention methods and more specifically to manufacture medical implants or medical devices with an anti-infective property in the most effective, accessible, flexible, cost-effective, and antimicrobial agent-compatible manner.

SUMMARY OF THE INVENTION

The disclosure provides methods of manufacturing anti-infective devices by mixing one or more antibacterial agents with one or more manufacturing materials in an ink composition prior to a device production. An object of the invention is a 3D printing ink composition that comprises a mixture of nitric oxide donors and polymers. One aspect of the disclosure provides an ink composition that includes a polymer or a polymer precursor, a nitric oxide donor and a catalyst or viscosity modifier. Another object of the invention provides methods of using such ink compositions for a 3D printer in the manufacture of a wide variety of medical devices. The invention provides superior efficiency over external coating or impregnation approaches in preserving the integrity of the nitric oxide donor material as well as the structural rigidity of a medical device. In the present invention, the nitric oxide donor may remain as fine powders and may not be dissolved in the polymer ink or in a solvent. By tuning the ink formulation, a low viscosity polymer can diffuse through a high viscosity polymer after the ink is printed and deposited, forming a protection layer on the outermost of the printed structures, which facilitates stable nitric oxide release rate. On the other hand, by utilizing a 3D printer with an adjustable parameter setting, a gradient of nitric oxide donor based on the complexity of shapes and geometries in the same device are also provided to sustain the nitric oxide release efficacy in any form or shaped devices.

In a particular preferred embodiment, the nitric oxide donor may be selected from S-nitrosothiols, diazeniumdiolates, organic nitrites, inorganic nitrosyl complexes, nitrite, sydnonimines, furoxans, hydroxyurea and/or combinations thereof. In some embodiments, the nitric oxide-releasing ink composition may comprise a polymer precursor or a polymer such as silicone rubber, polyurethane, polyether-block-amide, polyimide, nylon, polyethylene, polyether ether ketone, polycaprolactone, polyvinylidene fluoride, polytetrafluoroethylene and/or combinations thereof. In some embodiments, a nitric oxide-releasing catalyst (e.g., copper nanoparticle) and/or a polymer curing catalyst (e.g., platinum, tin) are added to the mixture.

Another aspect of the disclosure provides a method of manufacturing nitric oxide-releasing medical devices. In one embodiment, the method comprises steps of: i) loading the mixture of nitric oxide donor and polymer containing 3D printing ink composition onto an ink cartridge of a 3D printer; ii) receiving or retrieving a 3D model of a medical device with a printing parameter setting that assigns concentrations of the nitric oxide-releasing ink composition for all or some portions of the device; and iii) printing the nitric oxide-releasing medical device. In another embodiment, the method comprises additional steps of adjusting the printer parameter to have a spatial gradient of the nitric oxide-releasing ink composition so that the inner portion of the device has a higher concentration of the composition than in the outer portion of the device.

In some embodiments, nitric oxide and/or a nitric oxide donor may optionally be further combined with an agent or environment to aid the nitric oxide release. Examples include additional coating, impregnating and/or layering of the device with antimicrobial agents and/or other suitable hydrophilic coating vehicles and/or any material or combinations of materials that are compatible with the nitric oxide donor that may be subsequently or simultaneously applied with or manufactured with to ensure sufficient anti-infective action. In a preferred embodiment, this invention provides nitric oxide-releasing devices, which may be fabricated by direct ink writing 3D printing technology. Alternatively, other manufacturing techniques (e.g., cold extrusion process, fused deposition modeling, stereolithography, inkjet printing) may also be used.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

BRIEF DESCRIPTION OF THE DRAWINGS

FIG. 6A is a nitric oxide release measurement of S-nitrosoglutathione-loaded silicone rubber tube.

FIG. 6B is a nitric oxide release measurement of silicone rubber-PDMS tube.

DETAILED DESCRIPTION

Figure 1A:
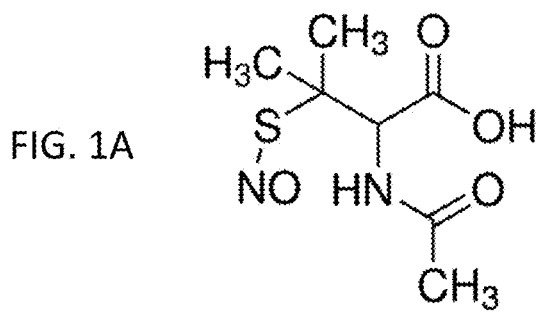
FIG. 1A is a chemical structure of the nitric oxide donor, S-nitroso-N-acetylpenicillamine.

The preferred embodiments of the present disclosure are directed toward nitric oxide donor containing 3D printing ink compositions and methods of using such compositions for manufacturing nitric oxide-releasing medical devices.

As used herein, a "medical device" is any device intended for medical purposes. Exemplary types of a medical device include an instrument, apparatus, constructed element or composition, machine, implement, or similar or related article that can be utilized to diagnose, prevent, treat or manage a disease or other conditions. The medical devices provided herein may, depending on the device and the embodiment, be implanted within a subject, utilized to deliver a device to a subject or utilized externally on a subject. The medical devices provided herein are sterile and are subject to regulatory requirements relating to their sale and use. Representative examples of medical devices and implants include, for example, cardiovascular devices and implants such as implantable cardioverter defibrillators, pacemakers, stents, stent grafts, bypass grafts, catheters and heart valves; orthopedic implants (e.g., total or partial arthroplastic joints such as hip and knee prosthesis); spinal implants and hardware (spinal cages, screws, plates, pins, rods and artificial discs); a wide variety of medical tubes, cosmetic and/or aesthetic implants (e.g., breast implants, fillers); a wide variety of polymers, bone cements, bone fillers, scaffolds, and naturally occurring materials (e.g., heart valves, and grafts from other naturally occurring sources); intrauterine devices; orthopedic hardware (e.g., casts, braces, tensor bandages, external fixation devices, tensors, slings and supports) and internal hardware (e.g., K-wires, pins, screws, plates, and intramedullary devices (e.g., rods and nails)); cochlear implants; dental implants; medical polymers, a wide variety of neurological devices; artificial intraocular eye lenses, skin dressings (e.g., wound care dressings), and wearable devices. In certain embodiments, the medical devices may also include a plurality of biomedical devices that are used in clinical and biomedical research settings (e.g., PCR machines or any other research instruments).

The medical device may include a sensor, which is defined herein as a device that can be utilized to measure one or more different aspects of a body tissue (anatomy, physiology, metabolism, and/or function) and/or one or more aspects of the medical device. Representative examples of sensors suitable for use within the present invention include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor or, within other embodiments, a sensor connected to a wireless microprocessor. Within further embodiments, one or more (including all) of the sensors can have a Unique Sensor Identification number ("USI") which specifically identifies the sensor and/or a Unique Device Identification number ("UDI") with which the sensors can provide unique information of the associated medical device for tracking purposes of the medical device manufacturer, the health care system, and regulatory requirements.

One aspect of the invention discloses a 3D printing ink composition for a medical device manufacture, and the composition comprises a nitric oxide donor as an antimicrobial agent. In certain embodiments, the nitric oxide donor is to produce nitric oxide, which exerts potent and broad-spectrum antibacterial activities via multiple nitrosylation and oxidation mechanisms toward enzymes, proteins, DNA, and lipids. Exogenous nitric oxide or in combinations with antibacterial or antimicrobial agents may further reduce the growth of multidrug-resistant bacteria in both planktonic and biofilm form. In some embodiments, the 3D printer ink composition comprises 0.1-15 wt %, preferably 0.2-13 wt %, more preferably 0.3-10 wt % of one or more nitric oxide donors.

As used herein, the term "nitric oxide donor," is a compound that contains a nitric oxide moiety, where the compound is able to release nitric oxide and/or chemically transfer the nitric oxide moiety to another molecule, directly or indirectly, for example, through a biological or chemical process. The nitric oxide donor may release nitric oxide, which may be bactericidal against various strains of bacteria, including both Gram-positive and Gram-negative organisms, fungi, mycobacteria, parasites, and viruses. Non-limiting examples of nitric oxide donors may include S-nitrosoglutathione (GSNO), arginine (e.g., L-arginine and/or D-arginine), arginine derivatives (e.g., L-arginine hydrochloride and/or D-arginine hydrochloride), nitroglycerin, polysaccharide-bound nitric oxide-nucleophile adducts, N-nitroso-N-substituted hydroxylamines, 1,3-(nitrooxymethyl)phenyl-2-hydroxybenzoate, etc. Additionally, the nitric oxide donor may be a polysaccharide-bound nitric oxide-nucleophile adduct, a N-nitroso-N-substituted hydroxylamines, a compound containing a sulfhydryl group and a NO donor group, 1,3-(nitrooxymethyl) phenyl-2-hydroxybenzoate, a gel comprising a nitrite salt and an acid, S-nitrosothiols, a nitrite, a 2-hydroxy-2-nitrosohydrazine, a substrate for nitric oxide synthase, a cytokine, an adenosine, bradykinin, calreticulin, bisacodyl, phenolphthalein, or endothelein. Further, non limiting examples of nitric oxide donors include a variety of S-nitrosothiol adduct, N-nitroso-N-(1-naphthyl) 15 hydroxylamine (ammonium or sodium salt), N-nitroso-N-(2-methylphenyl) hydroxylamine (salt), N-nitroso-N-(2-methoxyphenyl)-hydroxylamine (salt), N-nitroso N-(2-ethylphenyl)-hydroxylamine (salt), N-nitroso-N-(2-isopropylphenyl) hydroxylamine (salt), N-nitroso-N-(2, 4-difluorophenyl)-hydroxylamine (salt), N-nitroso N-(2, 5-difluorophenyl)-hydroxylamine (salt), N-nitroso-N-(2-chlorophenyl) 20 hydroxylamine (salt), N-nitroso-N-(2, 3-dichlorophenyl)-hydroxylamine (salt), N nitroso-N-(2, 4-dichlorophenyl)-hydroxylamine (salt), N-nitroso-N-(2, 5 dichlorophenyl)-hydroxylamine (salt), N-nitroso-N-(2-bromophenyl)-hydroxylamine (salt), N-nitroso-N-(5-fluoro-2-methylphenyl)-hydroxylamine (salt), N-nitroso-N-(4 fluoro-2-methylphenyl)-hydroxylamine (salt), N-nitroso-N-(4-choro-2-methylphenyl) 25 hydroxylamine (salt), or N-nitroso-N-(3-choro-2-methylphenyl)-hydroxylamine (salt). In some embodiments, a nitric oxide donor may also be chitosan, trans-1,2 dinitrato-4,5-dithiane; 2,2'-dithiodiethanol-dinitrate, 1,1-diemethanol-dinitrate-3,4-dithiane, 1,1'-bisthiomethyl-3,4-dihydroxy-cyclohexane-dinitrate ester, thiotyl alcohol nitrite ester, or 1,2-dihydroxy-dinitrate-6,8-dithiane, 1,3 (nitrooxymethyl)phenyl-2-hydroxybenzoate, nitroxide, sodium nitroprusside (Nipride), S nitroso-N-acetylpenicillamine (SNAP), 3-morpholino-synoniminhydrochloride (SIN-1), 3 15 morpholino-N-athoxycarbonly-syndnonimin (molsidomin), amyl nitrite (isoamyl nitrite), nitroglycerin (glyceryl trinitrite), isosorbide dinitrate (Isodil), isosorbide-5-monoitrite (Imur) or erythrityl tetranitrate (cardilate).

In some embodiments, the nitric oxide donor is mixed with a polymer or a polymer precursor in a 3D printing ink composition. In one embodiment, the polymer is a two-part silicone elastomer. As such, silicone polymer can be provided in a two-part silicone elastomer, monomer state and later polymerized, or in the alternative, provided in a polymerized state. In some embodiments, the 3D printer ink composition comprises 50-98 wt %, preferably 60-97 wt %, more preferably 70-95 wt % of silicone elastomer. In addition, still other materials can be used for the 3D printing ink composition, such as, but not limited to ceramic, glass, carbon (inclusive of nanotubes and graphite) and fabric. The silicone, ceramic, glass, carbon and fabric can be any appropriate particle forms and as are realized in the art and the choice generally relates, as with other materials used in the medical device, to the physical characteristics such as the ability to accept and retain a anti-infective agent (e.g., nitric oxide donor) for later release and the printing technology chosen to print the medical device. Preferable materials for the medical device include derivatized oligomers. Preferable derivatized oligomers include, but are not limited to HEMA (mydroxy ethylmethyl acrylates), DMA (dimethyl acrylamides), GMA (glycidol methyl acylates), PVA (polyvinyl alcohols), silicone or siloxane.

Alternatively, a plurality of other two-part silicone systems may be used, for example, the system with a part containing a polymer for enabling 3D printability and/or embedding the nitric oxide donor powder and/or any other anti-infective agents while another part contains a different type of polymer for providing a functional barrier coating on the printed structures may be used. The two types of polymers, agent-embedding polymer and coating polymer, may be mixed prior to subjecting the material to the processing operation at a fixed ratio of 1:30 to 1:1, preferably 1:25 to 1:2, more preferably 1:20 to 1:3 may be used. In some embodiments, the two-part silicone elastomer system comprises a condensation cure silicone or an addition cure silicone. In some embodiments, a weight ratio of a condensation silicone monomer to catalyst is about 20:1 to 10:1. In some embodiments, a weight ratio of an addition silicone monomer to catalyst is about 10:1 to 11:1.

Other examples of polymers, which may be mixed with nitric oxide donor in the ink composition may include, but are not limited to, polyethylene, polycarbonates, polyamides, polyesteramides, polyetheretherketone, polyacetals, polyketals, polyurethane, polyolefin, or polyethylene terephthalate and degradable polymers, for example, polylactide (PLA) including poly-L-lactide (PLLA), poly-glycolide (PGA), poly(lactide-co-glycolide) (PLGA) or polycaprolactone, caprolactones, polydioxanones, polyanhydrides, polyorthocarbonates, polyphospliazenes, chitin, chitosan, poly (amino acids), and polyorthoesters, and copolymers, terpolymers and combinations and mixtures thereof. Yet other examples of suitable polymers may also include synthetic polymers, for example, oligomers, homopolymers, and co-polymers, acrylics such as those polymerized from methyl cerylate, methyl methacrylate, acrylic acid, methacrylic acid, acrylamide, hydroxyethy acrylate, hydroxyethyl methacrylate, glyceryl scrylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrfluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyactic acid, polyglycolic acid, polydimethylsiloxanes, and polyetherketones. Additionally, a plurality of biodegradable polymers derived from natural sources such as modified polysaccharides (cellulose, chitin, chitosan, dextran) or modified proteins (fibrin, casein) may be used. Other examples of polymers may include synthetic polymers, for example, oligomers, homopolymers, and co-polymers, acrylics such as those polymerized from methyl cerylate, methyl methacrylate, acrylic acid, methacrylic acid, acrylamide, hydroxyethy acrylate, hydroxyethyl methacrylate, glyceryl scrylate, glyceryl methacrylate, methacrylamide and ethacrylamide; vinyls such as styrene, vinyl chloride, binaly pyrrolidone, polyvinyl alcohol, and vinyls acetate; polymers formed of ethylene, propylene, and tetrfluoroethylene. Further examples may include nylons such as polycoprolactam, polylauryl lactam, polyjexamethylene adipamide, and polyexamethylene dodecanediamide, and also polyurethanes, polycarbonates, polyamides, polysulfones, poly(ethylene terephthalate), polyacetals, polyketals, polydimethylsiloxanes, and polyetherketones. These examples of biodegradable polymers which may be utilized in addition to a preferred synthetic polymer and are not intended to be limiting or exhaustive but are intended to be illustrative of potential polymers which may be used. In these embodiments, the polymer of choice will be one capable of releasing nitric oxide. The polymer of choice may also depend upon the application in which polymer coating/film will be used and the desired nitric oxide release rate for that application. For example, a polymer having higher water uptake may be suitable in applications where quick nitric oxide release is desirable, while a polymer having lower water uptake may be suitable in applications where slow nitric oxide release is desirable.

In some embodiments, the one or more polymers comprise 5-40 wt % of one or more low viscosity silicone elastomers.

In accordance with the present invention, about 1-15 wt %, or preferably 2-12 wt %, or most preferably 3-10 wt % of catalyst (e.g., for polymerization and/or nitric oxide release) is added to the ink composition. Some exemplary catalysts include, but are not limited to, active or noble metal particles such as palladium, platinum, tin, silver particles and/or nanoparticles with a particle size of the catalyst preferably selected so that the particles are not to be so large as to interfere with the manufacturing process. Tin salts, copper salts, ZnO, thiols, ascorbic acid and combinations thereof may be used as catalysts. The catalyst may include $Al_2O_3$ dispersed in a mixture of $Cu(NO_3)_2$, hydroxypropyl methylcellulose and poly(ethylenimine). In some embodiments, to accelerate the curing process, diorganosulfoxides, imidazoles, and/or amines in combination with tin catalysts may be included. The ink composition presented herein may further include a bonding agent or crosslinking agent in order to aid in entrapping additional antimicrobials or otherwise immobilizing anti-infective agents for later release from the medical device. Exemplary bonding agents and crosslinking agents include, but are not limited to methylacrylic acid, titanates, silanes, HDI, derivitized oligomers of HEMA, GMA, DMA and PVA, polyfunctional aziridine, and multifunctional carbodiimide. Alternatively, useful compositions may further comprise conventional additives such as, for example, initiators, emulsifiers, stabilizers, antioxidants, flame retardants, adhesion promoters, release modifiers, colorants, thickeners, water scavengers, and the like.

In some embodiments, the nitric oxide donors may remain in fine powder form and are not dissolved in the polymer ink. Alternatively, the mixture composition is in their liquid states to form the ink for 3D printing. Further, additional solvent, carrier or particles may be incorporated to the composition to adjust the overall viscosity. Alternatively, the composition may be substantially or completely free of a UV initiator and/or a viscosity modifier, particularly in an embodiment when the ink composition was used for the direct ink writing printing process. As used herein, the term "substantially free" means less than 0.1 wt %. In other embodiments, the composition may be free of a UV initiator but contain one or more viscosity modifiers. Some exemplary viscosity modifiers include fumed silica, nanoclay and graphene nanoplatelets. In some embodiments, 0.05-20 wt %, preferably 0.08-15 wt %, more preferably 0.1-10 wt % of one or more viscosity modifiers may be included.

One aspect of the invention provides the method of using the ink composition described above for printing a nitric oxide-releasing medical device. The term "printing" described herein refers to the application of at least one printing formulation to a surface or a structure. Printing can use any appropriate device or method known in the art or later developed for a particular purpose. "3D printing" or "three-dimensional printing" refers to the printing of three-dimensional structures using appropriate printing technologies and printers as are known in the art. 3D printing is useful in the making of parts, products or layers using a computer driven, additive process, one or more layers at a time. 3D printing can build parts or other structures such as layers, using any appropriate material, such as, but not limited to plastic or metal, directly from CAD drawings or other digital images that have been preferably cross sectioned into many, if not hundreds or thousands of layers. 3D printing provides a faster and less costly alternative to machining, including but not limited to cutting, turning, grinding and drilling of materials, such as solid materials. Although various techniques are used in 3D printing in the relevant art, 3D printers use methods of additive fabrication, that is the building of a part or structure one layer at a time, with layers ranging in thickness from about a millimeter to less than $\frac{1}{1,000}$ of an inch. The building material can be in any appropriate form, such as, but not limited to a liquid, a powder or a sheet of material that is cured by heat, UV light, a chemical reaction or other appropriate method.

As a non-limiting introduction to digital printing methods and devices, the following 3D printing methods may be used: fused deposition modeling (FDM), direct ink writing (DIW), stereolithography (SLA), laminated object manufacturing (LOM), and selective laser sintering (SLS) ink jet printing. As such, a plurality of 3D manufacturing and curing methods (e.g., thermal, photo, chemical catalysis, etc.) may be utilized based on the intended uses and/or types of medical devices.

The preferred printing method, in some embodiments, is direct ink writing (DIW, also known to be analogous to robocasting). Generally, but not exclusively, a printing ink of the present invention replaces the UV-light curing methods of existing and commercially available printing devices, in particular, within the printing cartridge. Likewise, in a preferred embodiment, the silicone rubber polymer with a nitric oxide donor containing 3D ink composition is moisture-cured at 20-22° C. (68-72° F.) without any UV photo initiator.

DIW printing is known in the art and can take various forms and associated structures as are discussed herein and described in U.S. Pat. No. 6,027,326 to Cesarano III; incorporated by reference herein. The DIW refers to printing devices and methods that utilize highly precise printing methods and structures that allow to produce high quality and precise structures. Available DIW printing devices and structures can be utilized with minimal modification, with the ink solutions normally present in the 3D printer ink cartridge or reservoir is replaced with a solution that includes a polymerizable monomer and associated polymerization catalysts as needed. The polymerizable monomer can be polymerized at will and at a rapid rate after being dispensed from the DIW printing structure. Some of 3D printing techniques discussed herein are based primarily, but not exclusively, on liquid-based printing technologies. These methods and devices allow for the generation of one-off or multiple copies of a structure or structures. Generally, a polymerizable solution is placed within the printing device and is dispensed under computer control and polymerized in repeated printing cycles or steps to generate a 3D structure. Examples of available and preferred DIW 3D printing processes include, but are not limited to, dividing up a 3D CAD model into layers in a similar matter to other additive manufacturing techniques.

In aspects of the invention, a method of manufacturing a nitric oxide-releasing medical device comprises steps of: i) using an appropriate computer implemented software that is well known in the art to determine the three-dimensional design of the medical device; ii) loading an appropriate amount of the nitric oxide-releasing 3D printing composition onto an ink cartridge of a 3D printer; iii) receiving or retrieving a 3D model of a medical device with a printing parameter; iv) printing the medical device with the 3D printer. In some embodiments, an extrusion-based printing process (i.e. DIW) is used to extrude the ink material directly without melting or solidification. In these embodiments, the printing ink exhibits shear-thinning property that has a low viscosity to maintain its fluidity while being extruded out of the nozzle but after the extrusion, a high viscosity is achieved for the material to maintain its shape on the printing bed. In some embodiments, an ink contains one or more low molecular weight polymers (e.g., PDMS) with viscosities less than 10,000 cSt, preferably less than 5000 cSt, more preferably 1000-3000 cSt at 25° C. A surface coating layer is formed on the printed devices by a spontaneous diffusion of the low-viscosity silicone in the 3D printing composition. In some embodiments, a printing parameter setting may be set to include a printing speed of about 0.5-300 mm/s, preferably 0.8-250 mm/s, more preferably 1-200 mm/s. Further, in other embodiments, even lower viscosity polymers (viscosity range of about 50-200 cSt) may also be used. The printing parameter may also include an extrusion pressure of 0.05-14 bar, preferably 0.08-12 bar, more preferably 0.1-10 bar. In some embodiments, the printed medical devices may release anti-infective materials in the presence of moisture, chemical catalyst, heat or light. In other embodiments, the printing parameter may include a concentration setting of the 3D printing composition so that the concentration of the composition is uniform within the printed device. Alternatively, the printing parameter may be set to manufacture the medical device so that the 3D printing composition concentration is a compositional or functional gradient. In these embodiments, the inner portion of the device has a higher concentration of the composition than an outer portion of the device. In addition, in some embodiments, the printing method may further comprise a step of forming a surface coating layer by a spontaneous diffusion of the low-viscosity silicone in the 3D printing composition. In these embodiments, the low-viscosity silicone is in a weight ratio of about 10:1 to 1:1 with one or more catalysts used in the 3D printing composition.

Another 3D solid forming method, in some embodiments, is cold extrusion process. Generally, but not exclusively, an ink composite of the present invention replaces the typical materials of metals, polymers, ceramics, concrete, modeling clay of existing and commercially available cold extrusion devices, in particular, within the ink feeder. The ink material is pushed through a die of the desired cross-section, e.g. a tubular cross-section. Likewise, in preferred embodiments, the silicone rubber polymer with a nitric oxide donor containing 3D ink composition is moisture-cured at 20-22° C. (68-72° F.) after being extruded into devices of a fixed cross-sectional profile. In some embodiments, the method of cold extrusion process comprises multiple steps of loading an appropriate amount of the nitric oxide-releasing ink composition onto an ink cartridge of a cold extruder, pushing the ink through a die of the desired cross-section with a set extrusion parameter setting, and manufacturing a nitric oxide-releasing medical device. The term "die" used herein refers to a specialized tool used in extrusion-based printing or manufacturing to form or cut material to a desired shape or profile. A plurality of dies (e.g., stamping dies, drawing dies, casting dies, etc.) may be used for manufacturing nitric oxide releasing medical devices. Alternatively, any other extrusion processes known in the art (e.g., microextrusion, friction extrusion, warm extrusion, hot extrusion, etc.) may also be used with an effective temperature and/or curing time known in the art, which may be adjusted accordingly based on the volume, material and/or intended purposes of the 3D ink composition.

In preferred embodiments, the method of manufacturing a nitric oxide-releasing medical device may further comprise additional steps of controlling porosity on multiple scale levels to generate a scaffold structure with varying porosity that includes macroporosity (50-1000 microns), microprosity (1-50 microns) and nanoporosity (less than 1.0 micron). In addition, by controlling the material used, the pore structure, the strength of the scaffold and the sizes of the individual elements may be tailored based on the size and the volume of the medical devices. In the most preferred embodiment, the release rate of nitric oxide is controlled by creating compositionally and functionally graded nitric oxide donor and/or polymer composite structures. In some embodiments, additional steps of designing spatial optimization of donor concentration profile in forming gradient structures are included so that a lower concentration of the nitric oxide donor can be designed for the outer portion of the medical device and a higher concentration in the inner portion. Since the outer layer of the device may encounter more moisture while the inner layer may relatively be more protected, the distribution of high concentration of nitric oxide donor in the inner part of the device may enable a constant nitric oxide release rate over the entire intended period. Alternatively, the nitric oxide donor concentration gradient may be set to have the inner portion with a lower amount of nitric oxide donor and a higher amount in the outer portion of the device, in a particular condition where an initial burst of nitric oxide release is desired.

The nitric oxide-releasing medical device may have additional one or more layers to provide structural integrity and/or supplemental anti-infective property. Those layers which are designated for structural support may be formed from high-molecular weight polymers, e.g., PLLA or any other suitable polymer described herein, to provide a high degree of strength. The layers which are designated for supplemental anti-infective property may be placed within, upon, or between the structural layers or may be placed in the most outer portion of the device. In such a case, one embodiment includes an anti-infection agent and/or lubricious material on at least a portion of the additional layer. In this embodiment, an anti-infection agent and/or lubricious material may be disposed on or impregnated in at least a portion of a medical device. A lubricious material may be any material that when applied to an implantable medical device reduces the friction between the implantable medical device and the adjacent tissue. Any known or future developed lubricious material, or combinations thereof, may be used. Examples of suitable lubricous materials that may be disposed on at least a portion of a component of an implantable medical device include fluoroethylpolymer, polytetrafluoroethylene (PTFE), polyetheretherketone (PEEK), ethylene tetrafluoroethylene (ETFE), paralene, a hydrophilic polymer, and the like.

In another embodiment, the medical device may be placed into an anti-infection agent containing solution, allowing the anti-infection agent material to be retained on or become impregnated in the device. In these embodiments, any antimicrobial agent, such as an antibacterial agent, an antiseptic agent, etc., may be used to prevent infection. Nonlimiting examples of antiseptics include hexachlorophene, cationic biguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver sulfadiazine and alcohols. Nonlimiting examples of classes of antibiotics that may be used include tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem, aztreonam), aminoglycosides (e.g., gentamicin), chloramphenicol, sufonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole) and beta-lactam inhibitors (e.g., sulbactam). Nonlimiting examples of specific antibiotics that may be used include those listed above, as well as minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. The coatings can be applied to the surface of the device or an underlying coating layer through any coating processes known or developed in the art. By directly attaching a polymer coating to the outer portion of the device polymer layer, covalent chemical bonding techniques may be utilized. The manufactured medical device may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, and etching with strong organic solvents. Alternatively, the coating layer may be indirectly bound to the surface of the medical device or underlying coating layer through intermolecular attractions such as ionic or Van der Waals forces. An anti-infection agent may also be incorporated into a coating layer in a variety of ways. For example, anti-infection agent may be covalently grafted to a polymer of the coating layer, either alone or with a surface graft polymer. Alternatively, an anti-infection agent may be coated onto the surface of the polymer or member either alone or intermixed with an overcoating polymer. An anti-infection agent may be physically blended with a polymer of a coating layer as in a solid-solid solution. Anti-infection agent may be impregnated into a polymer by swelling the polymer or member in a solution of the appropriate solvent. Any means of incorporating anti-infection agent into or on a coating layer may be used, provided that anti-infection agent may be released, leached or diffuse from coating layer or the outer and inner surfaces of the device on contact with moisture and/or heat.

Alternatively, in some embodiments, a polymer of a coating layer and an anti-infection agent may be intimately mixed either by blending or using a solvent in which they are both soluble. This mixture can then be formed into the desired shape or coated onto an underlying structure of the medical device. Additionally, multiple layers of different antimicrobials may be loaded within the various layers. The manner and rate of the anti-infective agents (i.e. nitric oxide) release from multiple layers may depend in part upon the degradation rates of the substrate materials. For instance, polymers, which degrade relatively quickly may release antimicrobial agent layer-by-layer as each successive layer degrades to expose the next underlying layer. In other variations, drug release may typically occur from a multilayer matrix via a combination of diffusion and degradation.

In another embodiment, the polymeric substrate may be heated to increase its temperature along its entire length or along a selected portion of the substrate to a temperature that is at or above the $T_g$ of the polymer. For instance, for a substrate fabricated from PLLA, the substrate may be heated to a temperature between 60° C. to 70° C. In yet another embodiment, the polymeric substrate may be activated by UV light. In a preferred embodiment, the polymer is activated and cured by moisture in the air.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided it is understood that each intervening value, to the tenth of the unit of the lower limit unless the context clearly dictates otherwise, between the upper and lower limit of that range and any other stated or intervening value in that state range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

Example 1

3D Printing of SNAP-Doped Silicone Rubber Tubes
Ink Formulation

In these exemplary embodiments, the ink formulation consists of 2% NO donor (SNAP powder or GSNO powder) by weight in a silicone elastomer (Momentive). A sieve with 53 μm-pores was used to filter and remove any large NO donor particles to ensure a smooth printing process. The donor powder and silicone polymers were directly combined and mixed by a Thinky mixer (ARE-310) for 5 minutes at 2000 RPM. Defoam was proceeded for 30 seconds to remove any air bubbles inside the ink. Finally, about 0.6 grams catalyst was added and mixed with 10 grams composite. The final ink is transferred to an ink cartridge for printing.

Printing Process

Cylindrical tube structures were printed on a 3D printer (EnvisionTec, 3D Bioplotter) with the direct ink writing process. The tubes were modeled in a CAD software with dimensions of 7 mm in inner diameter, 9 mm in outer diameter, and 10 mm in height. A smooth-flow tapered nozzle (400 μm in diameter, Nordson) was used to print the drug-laden silicone tubes. To obtain the best printing quality, a series of printing parameters were determined in multiple sweeping tests, including 10 mm/s of printing speed, 170 kPa of extrusion pressure for ink formulation A, 150 kPa of extrusion pressure for ink formulation B, 0.2 s of pre-flow, and 0 s of post-flow, etc.

Nitric Oxide Release Measurement

NO release of the 3D printed tubes in phosphate buffered saline-EDTA (PBSE) at 37° C. was measured by an ECO PHYSICS NO analyzer (nCLD 66). Cylinders were tested by putting into an amber glass reaction cell containing 5 mL PBSE at 37° C. Nitrogen was used as the sweep gas to purge the released NO to the chemiluminescence detection chamber continuously. A mass-flow controller was used between the sample cell and the detector to maintain a flow rate of 100 standard cubic centimeters per minute (SCCM). SNAP-doped tubes were stored in PBSE at 37° C. between tests and fresh PBSE was used for storage after each NO release test. NO release from GSNO-doped tubes was measured continuously.

Optical Microscopy and Scanning Electron Microscopy

Luminal view and cross-sectional view of cylinder samples were inspected by a field-emission scanning electron microscope (FE-SEM, HITACHI, SU-70) with 5 kV operating voltage. The samples were sputtered with gold for 75 s (Denton Vacuum Desk V).

Antimicrobial Activities

Growth of bacterial biofilms on the 3D printed cylinders was tested using a previously described method with minor modifications. A single colony of *E. coli* was cultured overnight in liquid LB media at 180 rpm 30° C. Cylinders were sterilized by 70% ethanol for 15 min plus another 15 min UV exposure in a biosafety cabinet before being transferred into an autoclaved glass flask. 5 mL bacteria suspension and 45 mL ten-folded diluted broth (3.5 g/L LB or 0.8 g/L nutrient broth) were added to each flask. All glass flasks were incubated in a shaker for 24 h (200 rpm, 37° C.). The samples were aseptically removed from flasks and rinsed with sterilized DI water. Each cylinder was placed in 5 mL sterilized DI water and homogenized to disperse the biofilm. Then, the plate counting method was used to calculate the viable bacteria.

X-ray Diffraction Measurements

X-ray diffraction spectrums of blank silicone, SNAP-doped, and GSNO-doped cylinders were collected via Empyrean Multipurpose X-Ray Diffractometer with Copper Kα x-ray radiation at 40 kV and 40 mA. SNAP and GSNO powder patterns were integrated from 2.5° to 700 with a 0.1° step size and scan speed 0.5°/s on a reflection-transmission spinner stage. Cylinder samples were cut longitudinally and imaged on a 3-Axes cradle with auto chi, phi and Z stage. The patterns were integrated from 2.5° to 700 with a 0.010 step size and scan speed 0.015°/s.

Results and Discussion

3D Printing of SNAP-Doped Silicone Rubber Tubes

We have chosen the moisture-cured silicone materials due to their unique advantage of quick curing when exposed to ambient moisture. The surface of the printed 3D structures quickly becomes tacky (not fluidic anymore) immediately after they are deposited on the build plate through the layer-by-layer printing in ambient condition. The drastic increase in ink viscosity retains the shape and pattern of the devices.

Figure 1B:
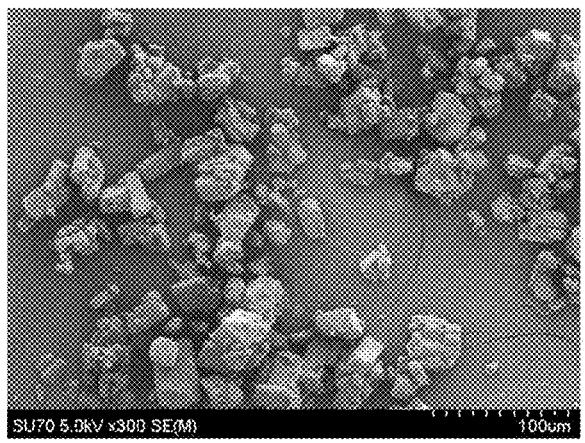
FIG. 1B is an SEM image of S-nitroso-N-acetylpenicillamine powder.
Figure 1C:
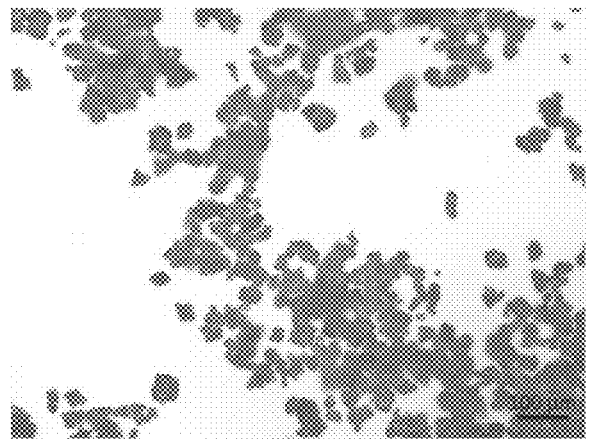
FIG. 1C is a bright-field image of S-nitroso-N-acetylpenicillamine powder.
Figure 1D:
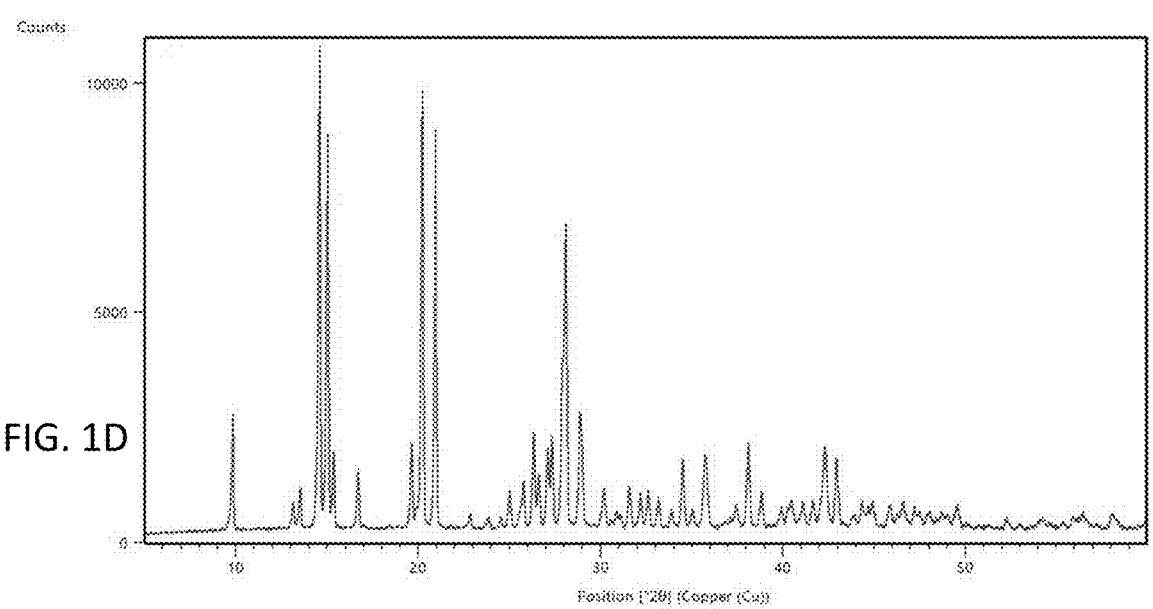
FIG. 1D is an X-ray diffraction pattern of S-nitroso-N-acetylpenicillamine powder.
Figure 3A:
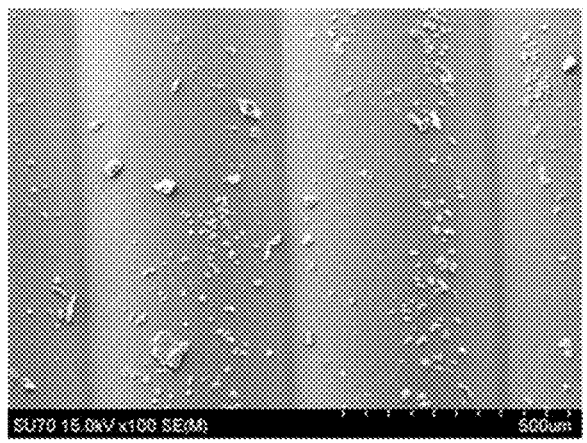
FIG. 3A-D is SEM images of the surface (A,B) and the cross-section (C,D) of the S-nitroso-N-acetylpenicillamine-doped silicone rubber tube before (A,C) and after (B,D) soaking.
Figure 3B:
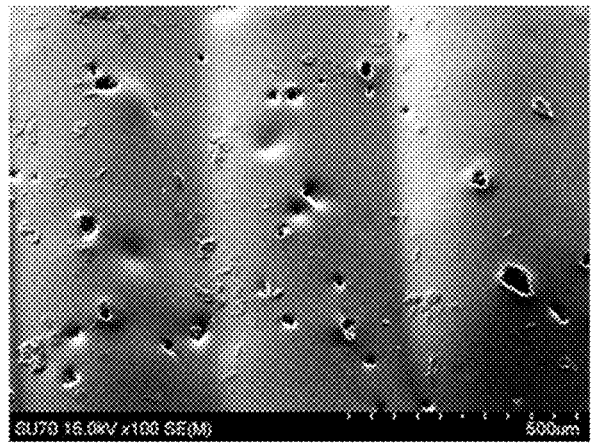
Figure 3C:
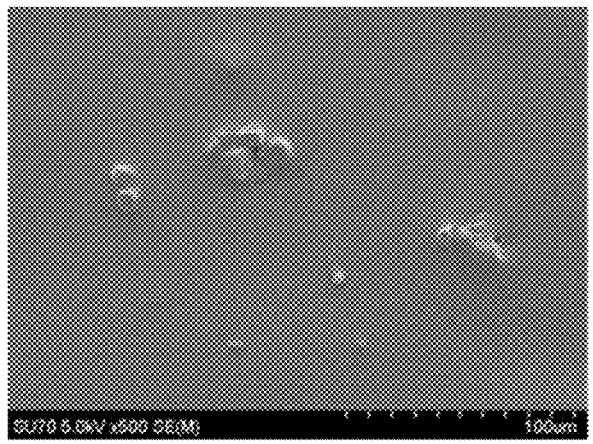
Figure 3D:
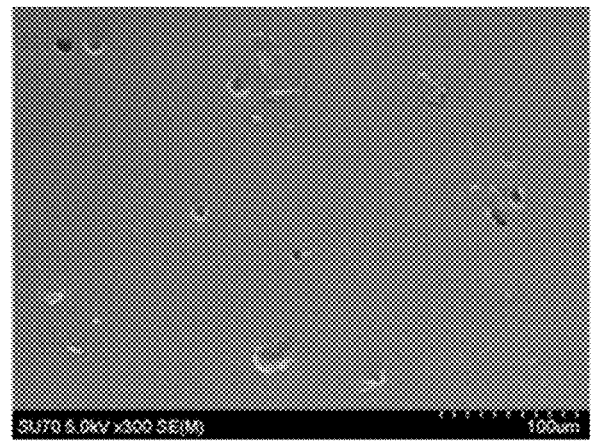

S-nitrosothiols have been widely used in medical devices to improve the device performance via release of nitric oxide. It has overall lower toxicity compared to donors like N-diazeniumdiolates. In our first trial, we mixed SNAP powders with silicone to formulate the inks. The SNAP powders used for ink formation are crystals ranging from 20 to 50 microns (FIGS. 1A and 1B, SEM and bright-field image). Crystallization is due to the strong intermolecular H-bonding (—OH and —NH as donors and C=O as acceptors of H-bonds) and the crystal structure is confirmed by the X-ray powder diffraction pattern (FIG. 1C). After mixing of SNAP crystals with silicone ink, the sizes of SNAP are not significantly changed (see FIG. 3B shown below), suggesting that SNAP crystals are not dissolved in the ink ingredients. XRD peaks can also be observed, but it is very week due to the low percentage of SNAP. Indeed, SNAP is most soluble in organic solvents such as methanol and tetrahydrofuran that are not present in the used ink.

Figure 2A:
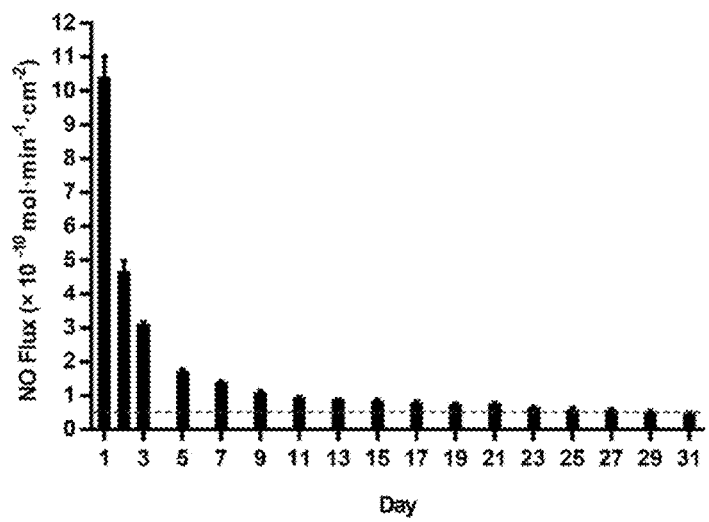
FIG. 2A is a nitric oxide release measurement of silicone rubber tube containing 2% S-nitroso-N-acetylpenicillamine at physiological temperature in phosphate buffered saline-EDTA.
Figure 2B:
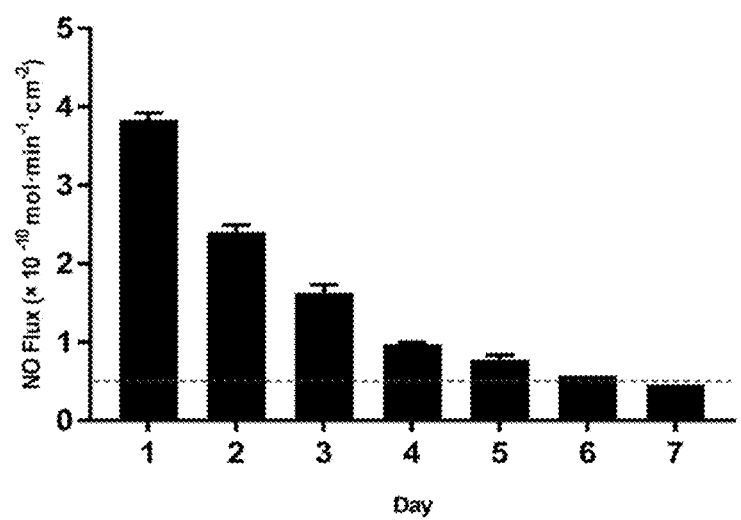
FIG. 2B is a Nitric oxide release measurement of silicone rubber tube containing 0.5% S-nitroso-N-acetylpenicillamine at physiological temperature in phosphate buffered saline-EDTA.

SNAP crystals do not release nitric oxide directly. Rather, they undergo slow dissolution in the presence of a small amount of absorbed water within the hydrophobic polymer and nitric oxide is released from decomposition of the dissolved SNAP. As shown in FIG. 2A, the tube with a 2 mm wall thickness releases nitric oxide of above $0.5 \times 10^{-10}$ mol $cm^{-2}$ $min^{-1}$ for 29 days at physiological temperature, which is among the most sustainable nitric oxide-releasing polymers including those based on silicone rubber. The $0.5 \times 10^{-10}$ mol $cm^{-2}$ $min^{-1}$ has been often used as a threshold level in nitric oxide-releasing medical devices because the endothelium of healthy blood vessels releases a nitric oxide surface flux of $0.5$-$4 \times 10^{-10}$ mol $cm^{-2}$ $min^{-1}$. The levels and durations of NO release can be further adjusted by using different ratios of nitric oxide donors in the polymer. For example, a 0.5% loading of SNAP allows release of nitric oxide above $0.5 \times 10^{-10}$ mol $cm^{-2}$ $min^{-1}$ for about 1 week (FIG. 2B). Although we did not systematically study the NO release profiles of different donor loading in this work, this pre-loading method allows facile and accurate control of drug loading compared to drug impregnation post device fabrication.

Figure 4A:
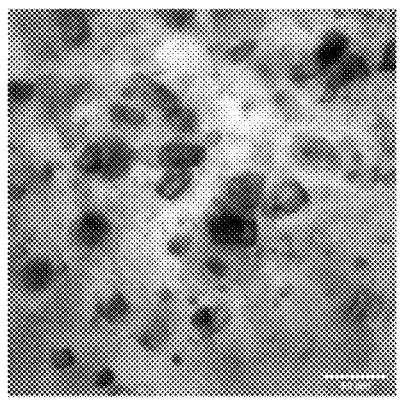
FIG. 4A-C is optical images of a thin layer of S-nitroso-N-acetylpenicillamine-doped silicone rubber before soaking (A) and after 24 h (B) and 48 h (C) of soaking in phosphate buffered saline-EDTA.
Figure 4B:
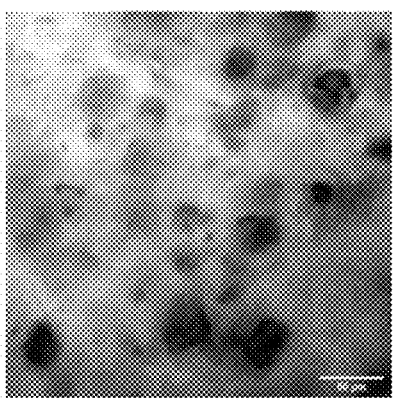
Figure 4C:
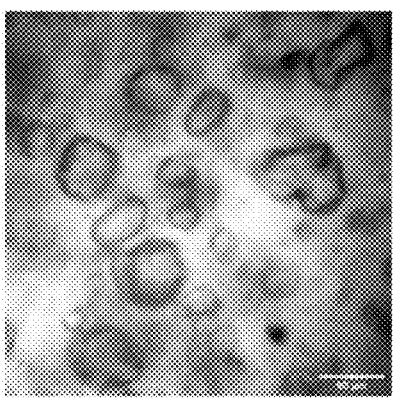

After dissolution of SNAP crystals and release of NO, holes may be formed in the place of crystals unless the decomposition products, namely N-acetyl-penicillamine (NAP) and NAP disulfide, fill the holes. SEM images of the surface and the inside of the polymer clearly show that holes are indeed formed throughout the polymer (FIG. 3). As shown in FIG. 4, the formation of holes is also observed in optical images of a thin layer of SNAP-doped silicone rubber (one layer of 3D printing).

Example 2

3D Printing of SNAP-Doped Silicone Rubber Tubes with a Drug-Free Coating Layer

Many NO donor-doped polymers have a burst release of NO upon initial soaking in a 37° C. solution. A topcoat of blank polymer without any NO donor has been applied to suppress this burst. Our 3D printed SNAP-doped silicone rubber also exhibits a higher NO flux in the first day. This is related to the SNAP particles on the surface that are directly exposed to the surrounding solution without any polymer encapsulation (FIG. 3A). These particles are easier to get dissolved or even drop into the solution, leading to the fast release of NO.

In previously published NO-releasing polymer devices, topcoats of polyurethane-based polymers have been obtained by dipping the device in an organic solution of a pure polymer. However, a thin and uniform layer of silicone coating is not easy to obtain on medical devices of various shapes. This is because silicone precursors are typically used without addition of extra solvents, in contrast to many thermoplastics that are readily dissolved in solvents and cure as coatings. 3D printing provided unique opportunities to generate an outmost silicone rubber layer on drug-loaded silicone devices to prevent drug leaching. One interesting method is the spontaneous diffusion of a low-viscosity silicone material into the surface during 3D printing because this method generates coating without any extra step.

The ink formulation that enables a drug-free coating layer on the printed structures contains the same weight percentage of SNAP powder (2%) in a mixture of silicone elastomers of polydimethylsiloxane (PDMS) and Momentive silicone. Specifically, the two-part PDMS according to the vendor's recommended ratio of (1:1) and the Momentive silicone monomer were mixed at the specified ratio of 1:9. Then 2 wt % of SNAP powder was added to the mixture of the silicones. The donor powder and silicone polymers were directly combined and mixed by a Thinky mixer (ARE-310) for 5 minutes at 2000 RPM. Defoam was proceeded for 30 seconds to remove any air bubbles inside the ink. Finally, about 0.5-0.6 grams catalyst was added and mixed with 10 grams composite. The final ink is transferred to an ink cartridge for printing.

Figure 5A:
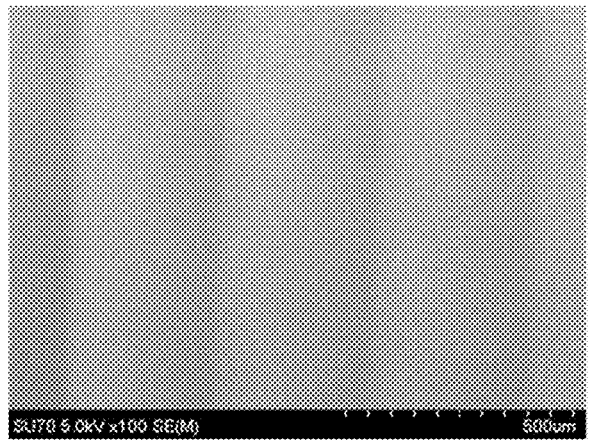
FIG. 5A-B is a SEM image of S-nitroso-N-acetylpenicillamine-doped silicone rubber-PDMS tube (A) before and (B) after soaking in phosphate buffered saline-EDTA.
Figure 5B:
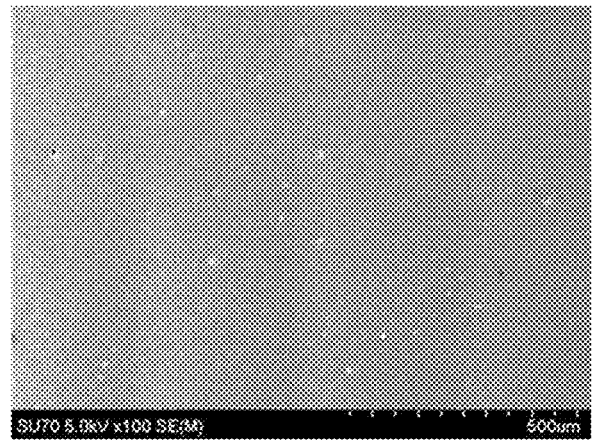
Figure 5C:
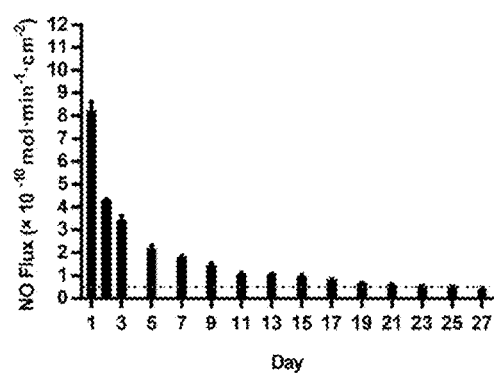
FIG. 5C is a nitric oxide release measurement of the tube shown in FIG. 5A.

As shown in FIG. 5A-B (SEM), the surface smoothness of tube is tremendously improved when 10% PDMS is added in the silicone ink, confirming the diffusion of PDMS onto the surface during printing. The smoother surface is highly desirable in medical applications. The NO release of the 2% SNAP-doped silicone rubber tube with PDMS is shown in FIG. 5C. The initial NO flux is indeed lower because of PDMS (10.4 vs. 8.2 on day 1). Increase of PDMS to 20% further reduces the NO flux to 4.8 on day 1, which is close to the upper end of the physiological level in blood vessels. However, the use of 20% PDMS causes a challenge in maintaining the designed 3D shapes on the printed structures due to the decrease in ink viscosity and delayed moisture curing. Therefore, 10% PDMS is selected in this work. With this concept demonstrated, we will examine other low-viscosity silicone recipes in the future to further suppress the initial burst release of NO without comprising the printing integrity. The use of a diffusive polymer in the ink substantially improves the surface smoothness and reduces the generation of pores in the polymer surface during use. This improved surface is critical in a wide variety of applications including anti-infection applications. Indeed, poorly defined porous structures may induce bacteria colonization or cell deposition.

Example 3

3D Printing of GSNO-Loaded Silicone Rubber Tubes

Figures 7A, 7B, 7C:
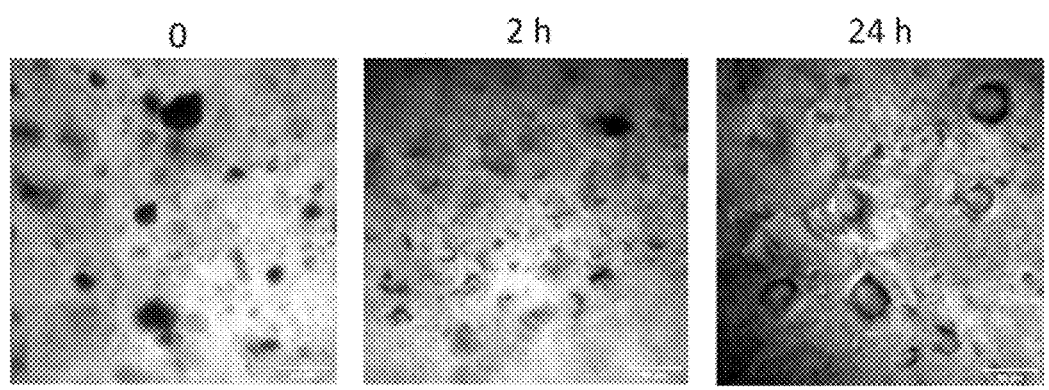
FIG. 7A-C is bright-field optical images of a thin layer of S-nitrosoglutathione-loaded silicon rubber before and after soaking in phosphate buffered saline-EDTA.

GSNO is a major endogenous NO carrier and donor in human body. Therefore, the use of GSNO as an exogenous NO source in medical devices will least likely cause concerns on drug toxicity unless the concentration is unreasonably high. Although SNAP has been introduced into a large variety of polymers via solvent-assisted impregnation, loading of GSNO into medical devices has been a challenge. This is because that GSNO is only appreciably dissolved in water and DMSO rather than organic solvents that can swell hydrophobic polymers used in indwelling devices. In contrast, our ambient 3D printing protocol is a generic fabrication method for silicone rubber mixed with any drugs. GSNO is also not soluble in the silicone rubber ink. We explored this direction using GSNO-loaded silicone rubber with and without 20% PDMS following the similar protocol of preparing the printing inks. As shown in FIG. 6, both tubes release nitric oxide above 0.5 for about 3 days. The smaller noise in the presence of PDMS is again confirming the protective function of the diffused PDMS on the surface, which is consistent with the SEM images. The much faster NO release is ascribed to the much higher water solubility of GSNO relative to SNAP. Indeed, according to optical images (FIG. 7), GSNO particles in the thin printed layer are dissolved within a day, which is much shorter than the 3 days required for dissolution of SNAP powders. Development of silicone materials with a lower water uptake is expected to reduce the drug dissolution and prolong the NO release.

What is claimed is:

1. A nitric oxide-releasing 3D printing composition comprising:
   0.3-10 wt % of one or more nitric oxide donors;
   70-95 wt % of one or more polymers; and
   3-10 wt % of one or more catalysts; or
   0.1-10 wt % of one or more viscosity modifiers,
   wherein the composition does not include fumed silica.

2. The 3D printing composition of claim 1, wherein the one or more nitric oxide donors are selected from the group consisting of S-nitrosothiol, diazeniumdiolate, S-nitroso-N-acetylpenicillamine, S-nitrosoglutathione, organic nitrite, inorganic nitrosyl complex, a nitrite ion, 3-morpholino-sydnonimine hydrochloride, furoxan, hydroxyurea, and any combinations thereof.

3. The 3D printing composition of claim 1, wherein the one or more polymers are selected from the group consisting of silicone rubber, polyurethane, polyether-block-amide, polyimide, nylon, polyethylene, polyether ether ketone, polycaprolactone, polyvinylidene fluoride, polytetrafluoroethylene, and any combinations thereof.

4. The 3D printing composition of claim 1, wherein the one or more polymers are in a two-part silicone elastomer system.

5. The 3D printing composition of claim 4, wherein the two-part silicone elastomer system comprises a condensation cure silicone or an addition cure silicone.

6. The 3D printing composition of claim 4, wherein a weight ratio of the one or more polymers to catalyst is about 20:1 to 1:1.

7. The 3D printing composition of claim 1, wherein the one or more polymers comprise 5-40 wt % of one or more low viscosity silicone elastomers.

8. The 3D printing composition of claim 1, wherein the one or more catalysts are metal or metal alloys in particulate form.

9. The 3D printing composition of claim 8, wherein the metal or metal alloys are active metals or noble metals.

10. The 3D printing composition of claim 8, wherein the metals are copper, palladium, platinum, or silver.

11. The 3D printing composition of claim 1, wherein the one or more catalysts are tin salts, copper salts, ZnO, thiols, ascorbic acid or combinations thereof.

12. The 3D printing composition of claim 1, wherein the one or more viscosity modifiers are selected from nanoclay and graphene nanoplatelets.

13. The 3D printing composition of claim 1, wherein the composition is substantially free of a UV initiator.

14. A method of manufacturing a nitric oxide-releasing medical device, comprising the steps of:
   loading an appropriate amount of the nitric oxide-releasing 3D printing composition of claim 1 onto an ink cartridge of a 3D printer;
   receiving or retrieving a 3D model of a medical device with a printing parameter setting, wherein the parameter setting defines a concentration of the 3D printing composition for an assigned region of the medical device; and
   printing a nitric oxide-releasing medical device with the 3D-printer.

15. The method of claim 14, wherein the 3D printer uses a processing technique of fused deposition modeling (FDM), direct ink writing (DIW) or laminated object manufacturing (LOM).

16. The method of claim 14, wherein the 3D printer uses a direct ink writing (DIW) technique.

17. The method of claim 14, wherein the appropriate amount of the nitric oxide-releasing 3D printing composition of claim 1 is determined based on a size and a volume of a medical device.

18. The method of claim 14, wherein the 3D printing composition concentration is uniform within the device.

19. The method of claim 14, wherein the 3D printing composition concentration is a compositional or functional gradient.

20. The method of claim 19, wherein an inner portion of the device has a higher concentration of the composition than an outer portion of the device.

21. The method of claim 14, wherein the method further comprises a step of forming a surface coating layer by a spontaneous diffusion of a low-viscosity silicone in the 3D printing composition.

22. The method of claim 14, wherein the method does not comprise a step of UV-light-activation to cure the 3D printing composition.

23. The method of claim 14, wherein the method further comprises a step of curing the 3D printing composition by moisture or by heat.

24. The method of claim 14, wherein the printer parameter setting further comprises a printing speed of about 1-200 mm/s.

25. The method of claim 14, wherein the printer parameter setting further comprises an extrusion pressure of 0.1-10 bar.

26. The method of claim 14, wherein the medical device releases nitric oxide in the presence of moisture, chemical catalyst, heat, or light.

27. The method of claim 14, wherein the method further comprises a step of printing, coating, or impregnating one or more layers of the medical device with one or more antimicrobial agents.

28. A nitric oxide-releasing medical device manufactured by the method of claim 14.

29. A method of manufacturing a nitric oxide-releasing medical device, comprising the steps of:
   loading an appropriate amount of the nitric oxide-releasing 3D printing composition of claim 1 onto an ink cartridge of a cold extruder;
   pushing the ink composition through a die, wherein the die is selected based on a shape of the nitric oxide-releasing medical device; and
   manufacturing the nitric oxide-releasing medical device with a fixed cross-sectional profile.

30. The method of claim 29, wherein the appropriate amount of the nitric oxide-releasing 3D printing composition is determined based on a size and a volume of a medical device.

31. The method of claim 29, wherein the concentration is uniform within the manufactured devices.

32. The method of claim 29, wherein the method does not comprise a step of UV-light-activation to cure the 3D printing composition.

33. The method of claim 29, wherein the method further comprises a step of curing the 3D printing composition by moisture or by heat.

34. The method of claim 29, wherein the extrusion parameter setting further comprises an extrusion speed of about 1-200 mm/s.

35. The method of claim 29, wherein the extrusion parameter setting further comprises an extrusion pressure of 0.1-10 bar.

36. The method of claim 29, wherein the medical device releases nitric oxide in the presence of moisture, chemical catalyst, heat, or light.

37. The method of claim 29, wherein the method further comprises a step of forming a surface coating layer by a spontaneous diffusion of a low-viscosity polymer in the 3D printing composition.

38. The method of claim 29, wherein the method further comprises a step of coating, or impregnating one or more layers of the medical device with one or more antimicrobial agents.

39. A nitric oxide-releasing medical device manufactured by the method of claim 29.

* * * * *